(12) United States Patent
Silva et al.

(10) Patent No.: US 11,337,740 B2
(45) Date of Patent: May 24, 2022

(54) BONE PLATE AND METHOD FOR USE IN A TIBIAL PLATEAU LEVELING OSTEOTOMY (TPLO)

(71) Applicant: OsteoCertus, LLC, Pembroke Pines, FL (US)

(72) Inventors: Cesar Silva, Pembroke Pines, FL (US); Javier E. Castaneda, Miami, FL (US)

(73) Assignee: OsteoCertus, LLC, Pembroke Pines, FL (US)

( * ) Notice: Subject to any disclaimer, the term of this patent is extended or adjusted under 35 U.S.C. 154(b) by 108 days.

(21) Appl. No.: 16/862,277

(22) Filed: Apr. 29, 2020

(65) Prior Publication Data
US 2021/0338293 A1    Nov. 4, 2021

(51) Int. Cl.
| | | |
|---|---|---|
| *A61B 17/80* | (2006.01) | |
| *A61D 1/00* | (2006.01) | |
| *A61B 17/16* | (2006.01) | |
| *A61B 17/84* | (2006.01) | |

(52) U.S. Cl.
CPC ...... *A61B 17/8061* (2013.01); *A61B 17/1662* (2013.01); *A61B 17/8014* (2013.01); *A61B 17/8052* (2013.01); *A61B 17/848* (2013.01); *A61D 1/00* (2013.01)

(58) Field of Classification Search
CPC . A61B 17/80; A61B 17/8014; A61B 17/8052; A61B 17/8057; A61B 17/8061; A61B 17/848; A61D 1/00
See application file for complete search history.

(56) References Cited

U.S. PATENT DOCUMENTS

| | | | |
|---|---|---|---|
| 7,635,381 B2 | 12/2009 | Orbay | |
| 10,149,708 B2* | 12/2018 | Kim | A61B 17/8052 |
| 10,226,288 B2 | 3/2019 | Sidebotham et al. | |
| 10,258,396 B2 | 4/2019 | Kazanovicz et al. | |
| 10,258,402 B2* | 4/2019 | Silva | A61B 17/8085 |
| 10,448,981 B2* | 10/2019 | Austin | A61B 17/8085 |
| 10,864,026 B2* | 12/2020 | Wotton, III | A61B 17/8057 |
| 2012/0265255 A1 | 10/2012 | Hilse et al. | |

OTHER PUBLICATIONS

"Clinical Application of the F3 Fragment Plating System in the Upper Extremity: A Series of Case Examples", David M. Huebner, MD et al, Biomet Orthopedics, 2012, Form No. BMET0017.0, REV060112.
"F3 Flexible Fragment Fixation Surgical Technique", Biomet Orthopedics, 2012, Form No. BME10013.0, REV053112.
"The Uses of the F3 Fragment Plating System in the Foot and Ankle", Mary Myerson, MD., Biomet Orthopedics, 2012, Form No. BMET0016.0, REV053112.

* cited by examiner

*Primary Examiner* — Larry E Waggle, Jr.
(74) *Attorney, Agent, or Firm* — Gordon & Jacobson, P.C.

(57) ABSTRACT

A tibial plateau leveling osteotomy (TPLO) system is provided for surgical correction of a stifle joint of an animal. The system includes a bone plate, fixed angle locking screw, compression screw, and a K-wire. The bone plate includes first surface and a second surfaces having common structure such that each can be positioned against the bone. The plate has a first shaft portion with a dynamic compression screw hole having a major length both extending along a first axis, and second shaft portion with a second axis and K-wire slot defining a major axis angled relative to the second axis but parallel to the first axis. The locking screw has double lead threads and the threaded holes in the plate have quad-lead threads.

18 Claims, 3 Drawing Sheets

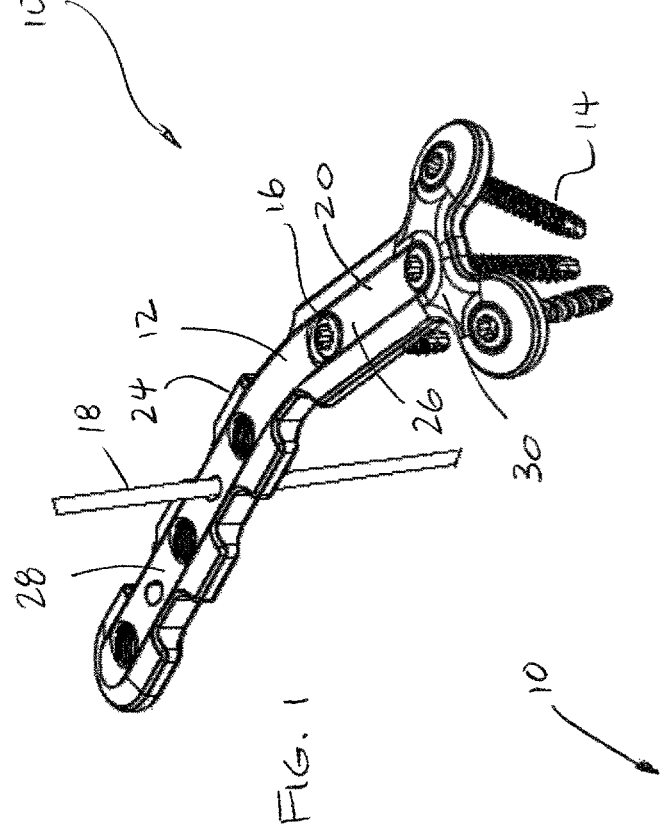
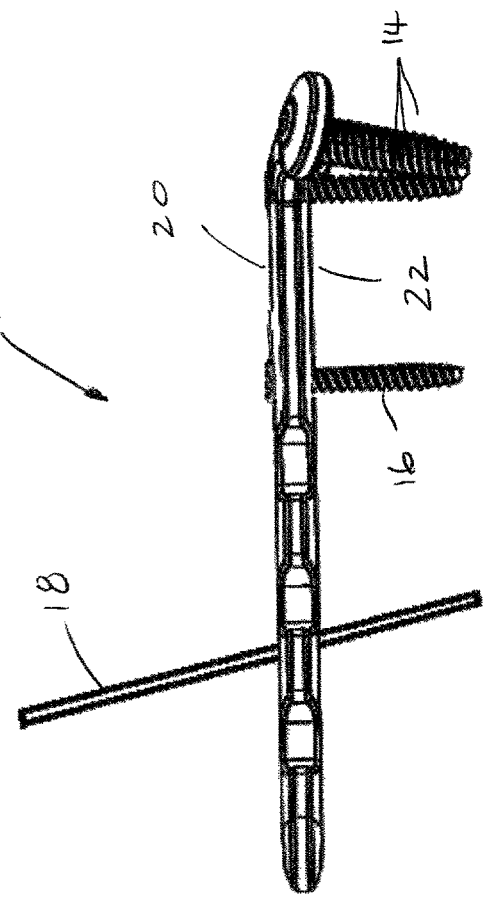
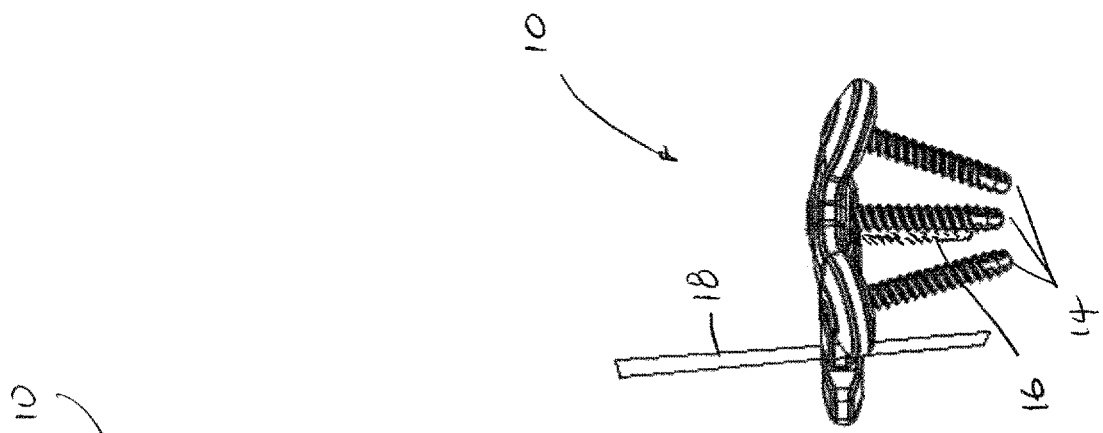

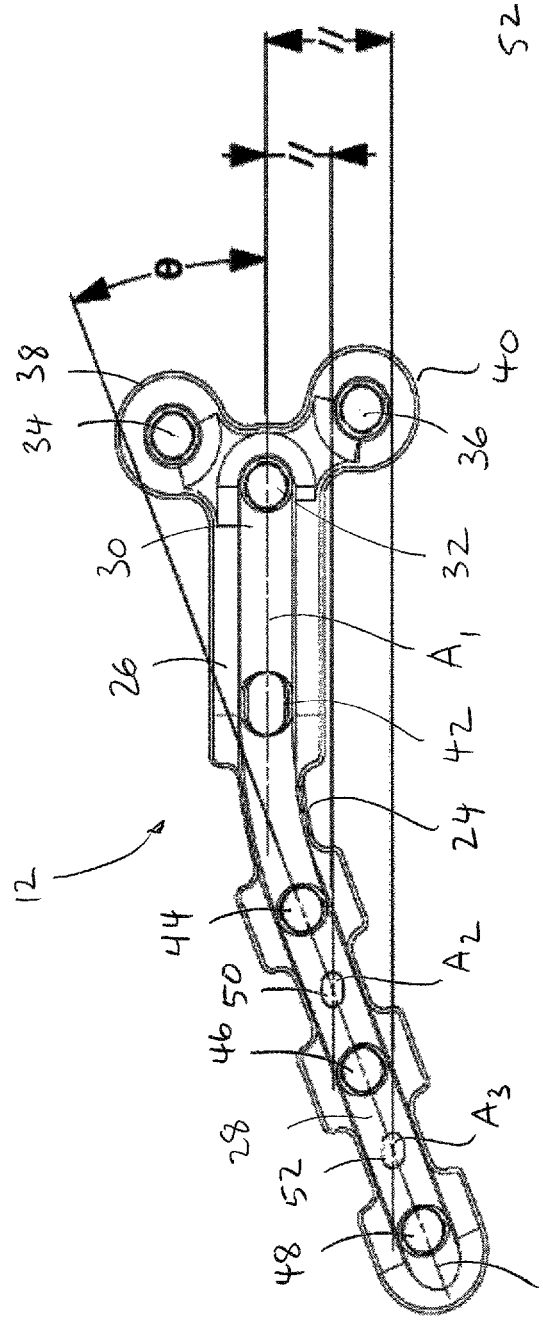
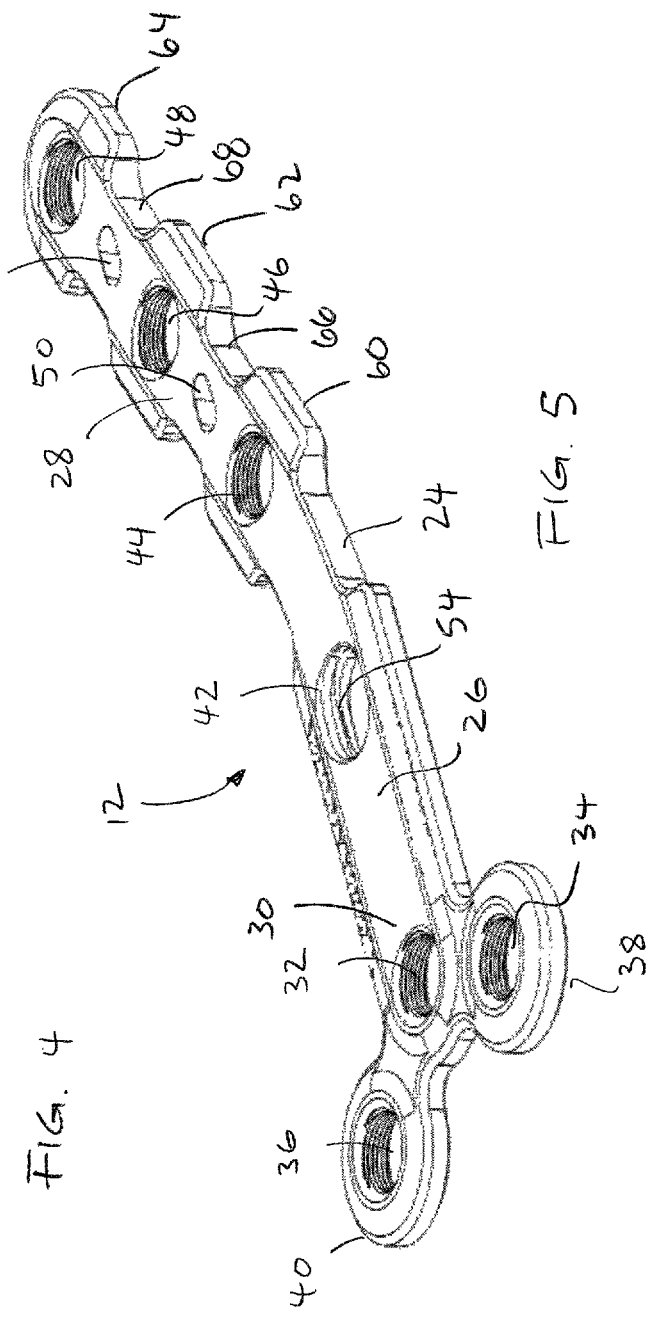

BONE PLATE AND METHOD FOR USE IN A TIBIAL PLATEAU LEVELING OSTEOTOMY (TPLO)

BACKGROUND OF THE INVENTION

1. Field of the Invention

The present invention relates to surgical implants and procedures. More particularly, the invention relates to veterinary orthopedic plates and methods of using such plates.

2. State of the Art

As a result of long-term degeneration, the cranial cruciate ligament (CrCL) in a dog can weaken over time. The cranial cruciate ligament runs from the cranial mid part of the tibial intercondylar eminence to the lateral condyle of the femur. Normally, the CrCL prevents caudal (backward) movement of the femur relative to the tibia. In various breeds, the tibial plateau acquires a caudal slope, so there is a constant stress on the cranial cruciate ligament. Over time this leads to a degenerative rupture. When the CrCL ruptures, the joint becomes unstable which causes pain and can lead to chronic progressive arthritis in the stifle if untreated.

Currently, a favored treatment for such condition is a tibial plateau leveling osteotomy (TPLO) procedure. In this procedure, an osteotomy is performed to cut through the tibial plateau, the portion of the tibia adjoining the stifle, and it is rotated to change the angle of contact between the between the femoral condyles and the tibial plateau. The cut is made in circular fashion so the osteotomized tibial plateau can be rotated and then secured with a bone plate in the new angle. The procedure typically requires pre and intra operative measurements to calculate and hopefully obtain the ideal angle of the tibial plateau. In an ideal angle, the tibial plateau is angled forward to reduce the tension in the anterior cruciate ligament (ACL) and avoid backward sliding of the femoral head due to gravity. The resulting re-aligned tibial plateau prevents the femur from sliding down the slope of the tibial plateau when the dog puts weight on its knee and provides the desired stability to the joint.

There are a variety of plates and instruments available in the market to perform this procedure. However, they are not ideal for obtaining accurate angular correction of the joint and optimal compression across the osteotomy. In addition, such plates are not optimized to provide a repeatable, precise, quick and systemic procedure.

SUMMARY OF THE INVENTION

A tibial plateau leveling osteotomy (TPLO) system is provided for surgical correction and stabilization of the stifle joint of a four-legged animal such as a dog. The system includes a bone plate, a plurality of bone anchors, and at least one K-wire.

The bone plate includes a first surface and a second surface opposite the first surface. The bone plate also includes a shaft with a first portion and second portion and head portion at an end of the first portion.

The head portion includes three threaded screw holes for receiving bone anchors inserted preferably along a predetermined and fixed axial trajectory defined by threads in the screw holes. One threaded screw hole is provided at or adjacent the intersection of the head portion with the first portion of the shaft. Second and third screw holes are arranged in ears that branch outward from the first portion of the shaft and which are bent relative to the head portion such that the screw holes define converging axes below the second surface (i.e., within the underlying bone).

The first and second surfaces, at at least the first and second portions of the shaft of the plate, have the same surface contours when viewed from the first and second surfaces such that each of the first and second surfaces thereat are reversibly configured for placement on a bone.

The first portion of the shaft has an oblong dynamic compression screw hole. The dynamic compression screw defines a major axis extending centrally along the first portion to intersect with the threaded screw hole in the head portion lying at or adjacent the intersection of the head portion with the first portion of the shaft.

The second portion of the shaft has at three threaded screw holes, respectively positioned in nodes, and two K-wire slots respectively positioned in intervening bridges. Each K-wire slot has a length longer than a width. The length defines a long axis extending substantially parallel to the major axis of the dynamic compression hole and the width is adapted in size to closely receive the K-wire.

Thus, the first shaft portion has an axis coaxial with the major axis of the dynamic compression screw hole, and the second shaft portion has an axis angled relative to the major axis. The K-wire slots each define a major axis that is parallel to the major axis but angled relative to the axis of the second shaft portion. In embodiments, the angle between the axes of the first and second portions of the shaft is between 10-35°, and more preferably about 22°.

In an embodiment, all screw holes, other than the dynamic compression screw hole, are circular threaded screw holes. In an embodiment, the circular threaded screw holes have a quad lead threading.

In an embodiment, a plurality of first bone anchors is provided for extension through the threaded screw holes. Each first bone anchor has a head and a shaft. The head includes at least one, preferably non-tapered, thread to engage each circular threaded screw hole in alignment with its respective axis. In an embodiment, the head has a two-start or two lead threads. With the head having one-half as many thread-starts as the screw holes have, the head of the bone anchor is both easier and quicker to engage in the screw hole than a fastener arrangement with an equal number of thread starts at both the screw and screw hole. The shaft of the bone anchor preferably includes a bone-engaging thread.

In an embodiment, a second bone anchor is provided for extension through the dynamic compression screw hole. The second bone anchor has a head adapted to seat on the rail within the dynamic compression screw hole. The shaft includes a bone-engaging cortical thread.

The system can be used in several ways to correct the stifle joint of a four-legged mammal. The stifle joint includes the distal end of the femur and the proximal end of the tibia. In some animals, the proximal end of the tibia defines a tibial plateau that is sloped sufficiently caudal to generate joint instability. To correct the instability, per standard procedure, a rotational cutter is used to cut an osteotomy through the tibia about a radius of curvature, thereby freeing the tibial plateau from the shaft of the tibia.

In one method, after cutting the osteotomy, the second portion of the shaft is temporarily fixed along the axis of the tibial shaft with at least one K-wire secured through one or more of the K-wire slots. This properly orients the head portion of the plate to engage the tibial plateau.

The tibial plateau is rotated as necessary to reorient the plateau to prevent slippage by the distal femur when under compression of the CrCL, and at least a first bone anchor is then inserted through one or more of the screw holes of the head portion of the plate to fix the plateau relative to the plate. In a preferred order, the tibial plateau is secured at the most-caudal screw hole first.

It is noted that the second portion of the shaft extends substantially transverse across the osteotomy cut line. Then, the second bone anchor is driven into the dynamic compression screw hole at its distal end (away from the head portion of the plate). As the head of the second bone anchor contacts the distal end of the dynamic compression screw hole, a force is applied to the plate that displaced the bone plate under the screw head and along the tibia. The displacement draws the tibial plateau attached to the head portion of the plate down against the tibial shaft and closes the osteotomy. The displacement is consistent in angle, always coaxial with the first portion of the shaft of the plate. Moreover, the angled long axis of the K-wire slot allows the shaft to move in the appropriate direction, with the length of the slot extending parallel to the axis of the first portion of the shaft. In addition, the slot length is sufficient for the plate displacement that occurs under dynamic compression. Then the second portion of the shaft of the plate is secured to the tibia with first bone anchors placed through the screws holes in the second portion. The K-wires are then removed. Additional first bone anchors are inserted through any remaining open screws holes.

The procedure may also be performed in a different sequence of surgical steps to correct the stifle joint, still taking advantage of features of the plate. For example, in another method of steps, after cutting the osteotomy, the head portion of the shaft is secured to the tibial plateau with one or more bone anchors extending through the screw holes in the head portion. The first portion of the shaft is then temporarily fixed along the axis of the tibial shaft with at least one K-wire secured through one or more of the K-wire slots. This rotates and reorients the tibial plateau into a desired orientation. The second portion of the shaft now extends substantially transverse across the osteotomy cut line.

Then, the second bone anchor is driven into the dynamic compression screw hole at its distal end (away from the head portion of the plate). As the head of the second bone anchor contacts the distal end of the dynamic compression screw hole, a force is applied to the plate that displaced the bone plate under the screw head and along the tibia. The displacement draws the tibial plateau attached to the head portion of the plate down against the tibial shaft and closes the osteotomy. The displacement is consistent in angle, always coaxial with the first portion of the shaft of the plate. Moreover, the angled long axis of the K-wire slot allows the shaft to move in the appropriate direction, with the length of the slot extending parallel to the axis of the first portion of the shaft. In addition, the slot length is sufficient for the plate displacement that occurs under dynamic compression. Then the first portion of the shaft of the plate is secured to the tibia with first bone anchors placed through the screw holes in the first portion. The K-wires are then removed. Additional first bone anchors are inserted through any remaining open screws holes.

BRIEF DESCRIPTION OF THE DRAWINGS

FIG. 1 is a top perspective of the TPLO bone plate system, partially provided with bone anchored and including a K-wire.

FIG. 2 is a side elevation of the TPLO bone plate system as shown in FIG. 1.

FIG. 3 is a front view of the TPLO bone plate system as shown in FIG. 1.

FIG. 4 is a plan view of a TPLO plate in one state of manufacture.

FIG. 5 is a top perspective view of the TPLO plate of FIG. 4.

DETAILED DESCRIPTION OF THE PREFERRED EMBODIMENTS

Figure 8:
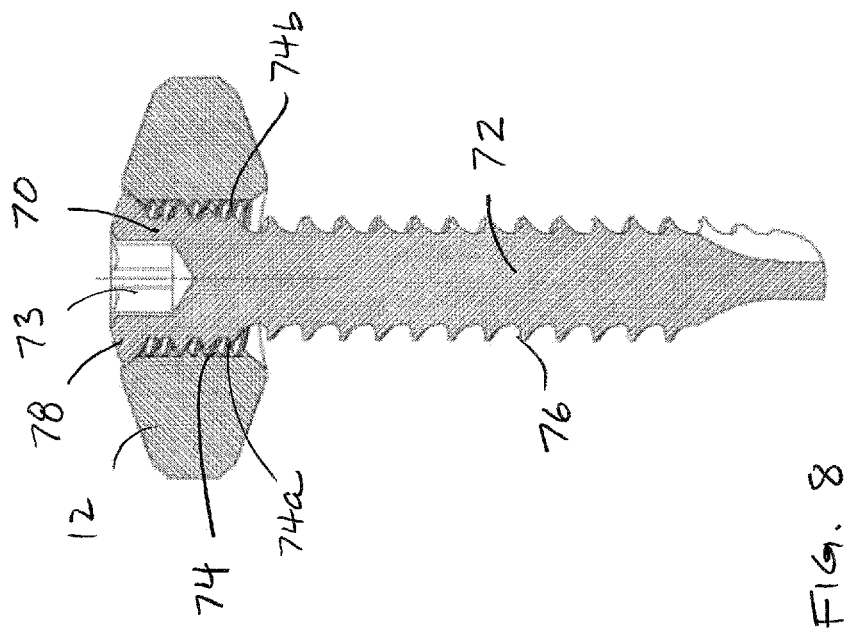
FIG. 8 is cross-sectional view across line 8-8 in FIG. 7.

Turning now to FIGS. 1 through 3, a tibial plateau leveling osteotomy (TPLO) plate system 10 is shown for use in surgical correction and stabilization of a stifle joint of a four-legged animal, such as a dog. The system 10 includes a bone plate 12, threaded head bone anchors 14, a dynamic compression anchor 16, and at least one K-wire 18.

Referring to FIGS. 1 through 5, the bone plate 12 includes a first surface 20 and an opposite second surface 22, each adapted for placement against an outer surface of an animal bone, as described below. The bone plate also includes a head portion 30 and a shaft 24, with the shaft having a first portion 26 and a second portion 28 laterally angled relative to each other by a nonzero angle. The head portion 30 extends from the first portion 26 of the shaft.

The head portion 30 preferably includes three threaded screw holes 32, 34, 36 for receiving threaded head bone anchors 14 inserted therein along a predetermined and fixed axial trajectory. One threaded screw hole 32 is provided at or adjacent the intersection of the head portion 30 with the first portion 26 of the shaft 24. Second and third screw holes 34, 36 are arranged in ears 38, 40 that branch outward from the first portion of the shaft. The ears 38, 40 are bendable relative to the head portion 30 and each other using appropriate bending tools. In a preferred manufactured configuration, as shown in FIGS. 1 through 3. The screw axes defined by the second and third screw holes 34, 36 converge toward each other below the surface of the plate intended for placement on the bone. For clarity, all screw holes in the plate 12 extend through the thickness of the plate, wherein the thickness is defined as the dimension of the plate extending between the first and second surfaces 20, 22.

The first portion 26 of the shaft 24 has an oblong dynamic compression screw hole 42 with a major diameter defining a major axis $A_1$ and a minor diameter (not shown) smaller than the major diameter that extends transverse to the major diameter. The major and minor diameters extend in a plane parallel to the first and second surfaces 20, 22 of the plate 12. The second portion 28 has three threaded screw holes 44, 46, 48 and two K-wire slots 50, 52 that also extend through the thickness of the plate. Each K-wire slot 50, 52 is oblong, having a length longer than a width. The length of slot 50 defines a long axis $A_2$, and the length of slot 52 defines a long axis $A_3$. The width of each slot 50, 52 is transverse to its respective long axis, and appropriately sized to closely receive the K-wire 18 so that the K-wire is stable in the slot 50, 52 in the widthwise direction; i.e., preferably without significant lateral displacement or wobbling. Axes $A_2$ and $A_3$ extend parallel to each other and the major axis $A_1$ of the dynamic compression hole 42.

The dynamic compression screw hole 42 in the first portion 26 is located at the opposite end of the first portion relative to the screw hole 32 of the head portion. In addition, the major diameter of the dynamic compression screw hole 42 preferably extends coaxial with the axis of the first portion of the shaft; such that axis $A_1$ is also the shaft axis of the first portion 26. Rails 54 are defined along the long sides of dynamic compression screw hole 42 (on opposing ends of, and extending transverse to, the minor diameter of the dynamic compression screw hole 42) equidistantly between the first and second surfaces 20, 22. The rails 54 allows screw hole to function as a dynamic compression hole regardless of which plate surface 20, 22 rest on the bone or interacting with compression screw 16 to effect dynamic compression.

In an embodiment, the second portion 28 of the shaft is defined by three longitudinally displaced nodes 60, 62, 64 connected by bridges 66, 68 (FIG. 5). The nodes 60, 62, 64 are bendable relative to each other, both laterally and medially relative to a longitudinal axis $A_4$ running along the second portion 28, and into and out of the plane of the plate, using appropriate bending tools. In one embodiment, each of the three nodes includes one of the screw holes 44, 46, 48, and each of the bridges between the nodes includes one of the K-wire slots 50, 52.

Thus, first shaft portion 26 has a longitudinal axis, and also includes dynamic compression screw hole 42 having a major diameter; both extend along axis $A_1$. Second shaft portion has axis $A_4$, and K-wire slots each define a major axis that is angled relative to axis $A_4$ but extends parallel to the axis $A_1$.

In an embodiment, all screw holes, other than the dynamic compression screw hole, are circular threaded screw holes. In an embodiment, the circular threaded holes have at more at than two thread starts, and preferably the quad lead threading, the use of which is described in more detail below.

In embodiments, axis $A_1$ extending through the first portion 26 of the shaft and axis $A_4$ extending through the second portion 28 of the shaft are laterally angled relative to each at angle θ, where θ is between 10°-35° (FIG. 4). In embodiments, θ is more preferably between 22.5°±2.5°. The first and second portions 26, 28 preferably extend within a common plane. However, the first and second portions 26, 28, or portions thereof, may be bent out of plane using suitable bending tools.

FIGS. 4 and 5, according to a preferred embodiment, show the plate in a first state of partial manufacture. Notice that at this state of manufacture, the ears 38, 40 of the head portion 30 extend in-plane with the shaft 24. Then, depending on whether the plate is designated to be a plate for treatment of the left or right stifle joint, it is preferable that at a subsequent stage of manufacture, the ears 38, 40 of the plate are bent out of plane (either away from the viewer in FIG. 4 for treatment of a right leg stifle joint to the eventual shape shown in FIGS. 1 to 3; or toward the view in FIG. 4 for treatment of a left leg stifle joint). In order to use a same first state of manufacture for a plate subsequently adapted to treat both left and right stifle joints, the first and second surfaces 20, 22 of the plate 12 must have the same surface contours when viewed from the first and second surfaces such that each of the first and second surfaces are reversibly configured with the same surface structure for placement directly on a bone with same effect. Thus, the first and second surface 20, 22 of the plate each have the same surface contours as described in detail in co-owned U.S. Pat. No. 10,258,402, which is hereby incorporated by reference herein in its entirety.

As an alternative manufacture, the plate 12 may be provided in the flat state (shown in FIGS. 4 and 5) as a final state of manufacture, and the ears of the plate may be subject to gross and/or fine bending prior to implantation at the intended stifle joint after the plate leaves the facility of manufacture. Such subsequent bending may occur, for example, in an operating room or other preparation area.

Figure 6:
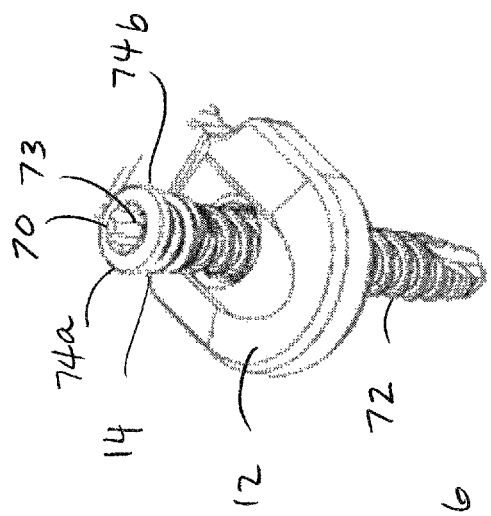
FIG. 6 is partial perspective of a dual lead thread bone anchor partially inserted into a quad lead screw hole in the TPLO plate.
Figure 7:
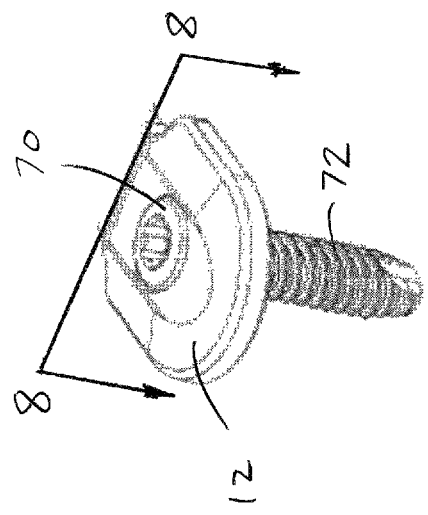
FIG. 7 is partial perspective of a dual lead thread bone anchor fully inserted into a quad lead screw hole in the TPLO plate.

Turning now to FIGS. 6 through 8, in an embodiment, the threaded head bone anchors 14 are provided for insertion through the quad-lead threaded screw holes in the plate and into underlying bone. Each bone anchor 14 has a head 70 and a shaft 72. The head 70 defines a central tool socket 73, an upper cap 78 that functions as a stop and at least one, preferably non-tapered, thread 74 to engage each circular threaded screw hole in the plate 12, in alignment with the respective axis defined by the threads about the screw hole. In a preferred embodiment, the head has two or more thread starts and most preferably two-start or two-lead threads 74a, 74b. With the head having one-half as many thread-starts as the screw quad lead threaded screw holes, the heads 70 of the bone anchor 14 are easier to orient and engage in the screw holes and are secured with fewer turns. In accord with the system, the thread starts for the threaded screw holes and the threads on the head of the bone are different, where the thread starts in the threaded screw holes is greater than two, and the thread starts on the bone anchor head is at least two.

The shaft 72 of the bone anchor preferably includes a bone-engaging thread 76. As shown at FIG. 8, the cap 78 of the head 70 preferably seats substantially flush with the surface of the plate facing outward from the bone when the head 70 of the anchor 14 is fully seated within its screw hole of the plate 12.

In an embodiment, the dynamic compression anchor 16 is provided for extension through the dynamic compression screw hole 42. The anchor 16 has a head adapted to seat on the rail 54 within the dynamic compression screw hole 42. The shaft includes a bone-engaging thread. The top of the head of the compression anchor 16 preferably seats substantially flush with the surface of the plate facing outward from the bone when the compression anchor 16 is fully seated within the compression screw hole 42 of the plate.

The system can be used in several ways to correct the stifle joint of a four-legged mammal. The stifle joint includes the distal end of the femur and the proximal end of the tibia. In some animals, the proximal end of the tibia defines a tibial plateau that is sloped sufficiently caudal to generate joint instability. To correct the instability, per standard procedure, a rotational cutter is used to cut an osteotomy through the tibia about a radius of curvature, thereby freeing the tibial plateau from the shaft of the tibia and permitting reorientation and fixation of the tibial plateau relative to the shaft of the tibia at a new angle rotated about the cut radius of curvature. The radius of the rotational cutter is selected by the veterinary surgeon based on the size of the head of the tibia.

In accord with one aspect of the method, the size of the TPLO plate to be used in the stifle joint correction is based on the radius of the rotational cutter used. This is different than prior methods. In prior methods, the size of the TPLO plate was selected based on the weight of the animal being surgically repaired. Thus, by way of example, a large, heavy canine would necessarily be selected to receive a large TPLO plate and a small, lighter canine would necessarily be selected to receive a small TPLO plate. This decision was made regardless of anatomical considerations of the joint. This was, in part, a necessity because prior art TPLO procedures failed to provide close approximation of the bone across the osteotomy and, thus, the TPLO plate bore the weight of the animal across a spaced-apart osteotomy during healing.

In distinction from such prior selection method, an embodiment of the instant method includes selecting the size of the TPLO plate based on the radius of the cutter used to define the angular osteotomy correction in the tibia. This is advantageous for at least several reasons. First, the size of the cutter is based on anatomical considerations at the joint, primarily the size of the tibial head; not the weight of the animal. Thus, animals having a large tibial head relative to their size will be selected for a larger plate, and animals having a smaller tibial head relative to their size will be selected for a smaller plate. Second, the plate is adapted to result in close approximation of the bone across the osteotomy. The K-wire slots permit required movement of the plate as the plate allows the bone at the osteotomy to undergo dynamic compression, and the plate, initially fixated at the K-wire slots, to appropriately move relative to those slots under such compression. Also, the plate incorporates, by design, a geometry of screw holes and shaft angles that is adapted to accommodate close approximation of the bone as the osteotomy is reduced. The hole locations on the angled portions of the plate are optimized in a plate for the radius of curvature of the cut by the cutter. This different approach to plate selection is possible at least in part because the plate pulls the osteotomy shut and leaves no (or practically no) gap at the osteotomy. Thus, rather than have a plate designed to carry the weight of the animal, the bone carries the weight, with the plate optimized to simply secure the bone portions together in the correct anatomical orientation.

In one method, after cutting the osteotomy, the second portion of the shaft is temporarily fixed along the axis of the tibial shaft with at least one K-wire secured through one or more of the K-wire slots. This properly orients the head portion of the plate to engage the tibial plateau.

The tibial plateau is rotated as necessary to reorient the plateau to prevent slippage by the distal femur when under compression of the CrCL, and at least a first bone anchor is then inserted through one or more of the screw holes of the head portion of the plate to fix the plateau relative to the plate. In a preferred order, the tibial plateau is secured at the most-caudal screw hole first.

It is noted that the second portion of the shaft extends substantially transverse across the osteotomy cut line. Then, the second bone anchor is driven into the dynamic compression screw hole at its distal end (away from the head portion of the plate). As the head of the second bone anchor contacts the distal end of the dynamic compression screw hole, a force is applied to the plate that displaced the bone plate under the screw head and along the tibia. The displacement draws the tibial plateau attached to the head portion of the plate down against the tibial shaft and closes the osteotomy. The displacement is consistent in angle, always coaxial with the first portion of the shaft of the plate. Moreover, the angled long axis of the K-wire slot allows the shaft to move in the appropriate direction, with the length of the slot extending parallel to the axis of the first portion of the shaft. In addition, the slot length is sufficient for the plate displacement that occurs under dynamic compression. Then the second portion of the shaft of the plate is secured to the tibia with first bone anchors placed through the screws holes in the second portion. The K-wires are then removed. Additional first bone anchors are inserted through any remaining open screws holes.

The procedure may also be performed in a different sequence of surgical steps to correct the stifle joint, still taking advantage of features of the plate. For example, in another method of steps, after cutting the osteotomy, the head portion of the shaft is secured to the tibial plateau with one or bore bone anchors extending through the screw holes in the head portion. The first portion of the shaft is then temporarily fixed along the axis of the tibial shaft with at least one K-wire secured through one or more of the K-wire slots. This rotates and reorients the tibial plateau into a desired orientation. The second portion of the shaft now extends substantially transverse across the osteotomy cut line.

Then, the second bone anchor is driven into the dynamic compression screw hole at its distal end (away from the head portion of the plate). As the head of the second bone anchor contacts the distal end of the dynamic compression screw hole, a force is applied to the plate that displaced the bone plate under the screw head and along the tibia. The displacement draws the tibial plateau attached to the head portion of the plate down against the tibial shaft and closes the osteotomy. The displacement is consistent in angle, always coaxial with the first portion of the shaft of the plate. Moreover, the angled long axis of the K-wire slot allows the shaft to move in the appropriate direction, with the length of the slot extending parallel to the axis of the first portion of the shaft. In addition, the slot length is sufficient for the plate displacement that occurs under dynamic compression. Then the first portion of the shaft of the plate is secured to the tibia with first bone anchors placed through the screw holes in the first portion. The K-wires are then removed. Additional first bone anchors are inserted through any remaining open screws holes.

There have been described and illustrated herein embodiments of a TPLO plate, a plate and bone anchor system, and methods of implanting the plate and system in an animal. While particular embodiments of the invention have been described, it is not intended that the invention be limited thereto, as it is intended that the invention be as broad in scope as the art will allow and that the specification be read likewise. Thus, while the dual lead thread anchors have been described for use in association with the quad lead anchor holes in the TPLO plate, it is recognized that this system for securing a bone anchor to a bone plate has application beyond TPLO, and beyond veterinary plates in general; this system may be applied to all orthopedic bone plates whether to treat trauma, correct anatomical deformities, correct defects of disease, or any other necessities for orthopedic treatment. In addition, while a specific number of shaft portions, nodes, bridges, screw holes, K-wire holes, etc. have been described in association with preferred plates, it is understood that the invention is not limited thereto. Also, while particular preferred angles have been described, which correspond to the 'best fit' angles for the plate on the bone at the time of filing, it is recognized that the invention is not limited thereto unless specifically incorporated into a claim. It will therefore be appreciated by those skilled in the art that yet other modifications could be made to the provided invention without deviating from its scope as claimed.

What is claimed is:

1. A bone plate for use with a K-wire in a tibial plateau leveling osteotomy (TPLO) to stabilize a stifle joint of a four-legged mammal, comprising:
   a top surface and a bottom surface opposite the top surface, a shaft with a first portion and a second portion laterally angled relative to each other, and a head extending from the first portion of the shaft, the head having at least one head screw hole for receiving a bone anchor, the first portion having an oblong dynamic compression hole with a major diameter defining a major axis along a longest length of the dynamic compression hole, and the second portion having at least one shaft screw hole and at least one K-wire slot, the K-wire slot having a length longer than a width, the length defining a slot axis extending substantially parallel to the major axis of the dynamic compression hole and the width adapted in size to closely receive the K-wire, the K-wire slot extending from the top surface completely through to the bottom surface along the length of the K-wire slot.

2. The bone plate of claim 1, wherein at least one of the head and shaft screw holes has quad lead threads.

3. The bone plate of claim 2, in combination with a bone anchor having a head with threads that consists of dual threads.

4. The bone plate of claim 1, wherein the first portion and the second portion are laterally angled relative to each at between 10°-35°.

5. The bone plate of claim 1, wherein the first portion and the second portion are laterally angled relative to each at 22.5°±2.5°.

6. The bone plate of claim 1, where the first and second portions extend within a common plane.

7. The bone plate of claim 1, wherein:
the bottom surface is for placement against the bone, and
the at least one head screw hole includes first and second head screw holes which have respective first and second fixed central axes extending through the first and second head screw holes of the plate, the first and second central axes converging toward each other.

8. The bone plate of claim 7, wherein the first and second fixed central axes are defined by threads extending about the first and second head screw holes.

9. A bone plate for use with a K-wire in a tibial plateau leveling osteotomy (TPLO) to stabilize a stifle joint of a four-legged mammal, comprising:
a top side and a bottom side opposite the top side,
a head portion having at least one threaded screw hole for receiving a bone anchor,
a shaft with a first portion having a first axis, and a second portion having a second axis, the first and second axis laterally angled relative to each other by a non-zero angle,
the first portion extending from the head portion and including a dynamic compression screw hole with a major diameter extending coaxial with the first axis,
the second portion having,
at least one screw hole, and
a K-wire slot having a width and a length longer than the width, the width sized to closely accommodate the K-wire, and the length defining a third axis,
wherein the third axis is parallel with the first axis and angled at the nonzero angle relative to the second axis.

10. The bone plate of claim 9, wherein the nonzero angle is between 10°-35°.

11. The bone plate of claim 9, wherein the nonzero angle is between 22.5°±2.5°.

12. The bone plate of claim 9, wherein the first and second portions of the shaft are in plane with each other.

13. A bone plate for use with a K-wire in a tibial plateau leveling osteotomy (TPLO) to stabilize a stifle joint of a four-legged mammal, comprising:
a top surface and a bottom surface opposite the top surface,
a head portion having a first threaded screw hole for receiving a bone anchor, and second and third screw holes,
a shaft with a first portion and a second portion laterally angled relative to each by an angle,
the first portion extending from the head portion and including a dynamic compression screw hole with a major diameter defining a first axis intersecting the first threaded screw hole, the second and third screw holes of the head portion located on opposite sides of the first axis,
the second portion having,
a plurality of screw holes spaced along a length of the second portion, defining a second axis between the plurality of screw holes, and
a K-wire slot having a width and a length longer than the width, the width sized to closely accommodate the K-wire, and the length defining a third axis,
wherein the second axis is angled relative to the first axis, and the third axis is parallel to the first axis.

14. The bone plate of claim 13, wherein the second axis is laterally angled by 10°-35° relative to the first axis.

15. The bone plate of claim 13, wherein the second axis is laterally angled by 22.5°±2.5° relative to the first axis.

16. The bone plate of claim 13, wherein the first and second portions of the shaft are in plane with each other.

17. The bone plate of claim 13, wherein the second and third screw holes are bent out of plane with the shaft.

18. The bone plate of claim 13, wherein at least one of:
a) the first threaded screw hole in the head portion, and
b) the plurality of screw holes in the second portion of the shaft, include quad lead threads.

* * * * *